United States Patent
O'Dea (10) Patent No.: US 8,845,582 B2
(45) Date of Patent: Sep. 30, 2014

(54) DEVICE FOR PROTECTING A CATHETER, AND A METHOD FOR LOCATING A CATHETER IN A REMOTE LOCATION IN A HUMAN OR ANIMAL BODY

(75) Inventor: John O'Dea, Bearna (IE)

(73) Assignee: Flip Technologies Limited, Galway (IE)

( * ) Notice: Subject to any disclaimer, the term of this patent is extended or adjusted under 35 U.S.C. 154(b) by 80 days.

(21) Appl. No.: 13/255,191

(22) PCT Filed: Mar. 9, 2010

(86) PCT No.: PCT/IE2010/000010
§ 371 (c)(1), (2), (4) Date: Nov. 4, 2011

(87) PCT Pub. No.: WO2010/103501
PCT Pub. Date: Sep. 16, 2010

(65) Prior Publication Data
US 2012/0065585 A1    Mar. 15, 2012

(30) Foreign Application Priority Data
Mar. 9, 2009    (IE) .................................. S2009/0183

(51) Int. Cl.
| | |
|---|---|
| A61M 29/00 | (2006.01) |
| A61B 1/00 | (2006.01) |
| A61M 25/06 | (2006.01) |
| A61M 25/10 | (2013.01) |
| A61M 25/01 | (2006.01) |
| A61M 25/00 | (2006.01) |
| A61B 19/00 | (2006.01) |
| A61M 25/09 | (2006.01) |

(52) U.S. Cl.
CPC ... *A61M 25/0111* (2013.01); *A61M 2025/0681* (2013.01); *A61M 2025/1081* (2013.01); *A61B 1/00142* (2013.01); *A61M 2025/0177* (2013.01); *A61B 1/00135* (2013.01); *A61M 25/0054* (2013.01); *A61B 19/38* (2013.01); *A61M 25/09* (2013.01)

USPC .................................. 604/103.05; 604/101.02

(58) Field of Classification Search
USPC ............ 604/96.01, 101.02, 103.05, 907, 915; 606/191–199
See application file for complete search history.

(56) References Cited

U.S. PATENT DOCUMENTS

| | | | |
|---|---|---|---|
| 4,338,942 A * | 7/1982 | Fogarty | ......................... 606/194 |
| 5,306,261 A | 4/1994 | Alliger et al. | |
| 5,360,401 A * | 11/1994 | Turnland et al. | ......... 604/103.05 |

(Continued)

FOREIGN PATENT DOCUMENTS

| | | |
|---|---|---|
| WO | 95/03082 A1 | 2/1995 |
| WO | 00/42900 A2 | 7/2000 |

(Continued)

OTHER PUBLICATIONS

International Search Report for PCT/IE2010/000010 dated Jun. 30, 2010.

*Primary Examiner* — Quynh-Nhu H Vu
(74) *Attorney, Agent, or Firm* — Sughrue Mion, PLLC (57) ABSTRACT

A device (1) comprises a sheath (9) for protecting a balloon catheter (2) from contamination with bodily fluids and other matter during the carrying out of a procedure or investigation at a remote site in a human or animal body. The sheath (9) defines a catheter accommodating portion (14) and a balloon accommodating portion (15) for accommodating a catheter (4) and a balloon (8) of the balloon catheter (2) therein. The sheath (9) is of a flexible material having a closed distal end (11) and a proximal opening (13) at a proximal end (10) thereof to a hollow interior region (12) within which the balloon catheter (2) is accommodated. A guide wire engaging distal portion (19) engages and locates a guide wire (7) within the sheath (9). The balloon accommodating portion (15) permits inflating of the balloon (8) to a predefined volume.

20 Claims, 7 Drawing Sheets

(56) References Cited

U.S. PATENT DOCUMENTS

| | | | |
|---|---|---|---|
| 5,406,939 A | 4/1995 | Bala | |
| 6,527,740 B1 * | 3/2003 | Jackson et al. | 604/103.05 |
| 6,923,827 B2 * | 8/2005 | Campbell et al. | 623/1.11 |
| 2005/0143625 A1 | 6/2005 | Whitmore, III et al. | |
| 2005/0182286 A1 * | 8/2005 | Lubock | 600/3 |

FOREIGN PATENT DOCUMENTS

| | | |
|---|---|---|
| WO | 03/024318 A1 | 3/2003 |
| WO | 03/090834 A2 | 11/2003 |
| WO | 2004/008950 A1 | 1/2004 |
| WO | 2007/028009 A1 | 3/2007 |

* cited by examiner

DEVICE FOR PROTECTING A CATHETER, AND A METHOD FOR LOCATING A CATHETER IN A REMOTE LOCATION IN A HUMAN OR ANIMAL BODY

BACKGROUND OF THE INVENTION

The present invention relates to a method and a device for protecting a catheter, and in particular, though not limited to a method and a device for protecting a balloon catheter during use of the catheter in a procedure, so that the catheter may be reused, and the invention also relates to a method for locating a catheter and a balloon catheter at a remote site, such as a remote site in a human or animal body with the catheters protected, so that the catheters may be reused.

Catheters are commonly used for gaining access to a remote site in a human or animal body, in order to facilitate the carrying out of a procedure or an investigation at the remote site. Access to the remote site is gained through a lumen, a vessel or a vascular system of the human or animal body, within which the remote site is located. For example, catheters are commonly used to gain access to the oesophagus, the lower oesophageal sphincter, the stomach and other parts of the digestive system of the human or animal body. Catheters for gaining access to the oesophagus, stomach and the like, typically are inserted nasally or orally into the oesophagus. Catheters are also used to gain access to remote sites in the bowel, large and small intestine, and in such cases, the catheter typically is rectally inserted. Catheters are also used to gain access to the uterus, the urinary tract and the like. Additionally, catheters are used to gain access to the vascular and cardiovascular system. All such catheters, in general, are used once and disposed of due to the difficulty in cleaning and sterilising such catheters after use, and in particular, cleaning and sterilising a lumen or lumens of such catheters which are exposed at, for example, a distal end of the catheter, such as a guide wire accommodating lumen. However, such catheters, in general, tend to be relatively expensive, and in general, balloon catheters are particularly expensive, in particular, balloon catheters which are adapted for determining the volume of a remote vessel or lumen, or for determining the transverse cross-sectional area or diameter and/or distensibility of a remote sphincter, vessel or lumen, tend to be particularly expensive. It would therefore be advantageous if such catheters could be reused.

It is, however, known to provide a protective sheath which extends over a catheter. Such a sheath is sold under the Trade Mark MANOSHIELD of Sierra Scientific Instruments. A catheter is threaded into the sheath prior to use, and on being fully inserted into the sheath, the sheathed catheter is then inserted into the appropriate lumen, vessel or vascular system of the human or animal body and directed towards a remote site at which a procedure or investigation is to be carried out. On completion of the procedure or investigation, the sheathed catheter is removed, and the sheath is then removed from the catheter. Thus, any bodily fluids or contaminants with which the sheathed catheter may have come into contact within the lumen, vessel or vascular system, and which may have adhered to the sheath are removed with the sheath as the sheath is being removed from the catheter. Thus, with the sheath removed, the catheter is clean and is ready for re-sheathing and reuse.

However, the sheath which is sold under the Trade Mark MANOSHIELD suffers from at least two problems. Firstly, the sheath is unsuitable for use with a balloon catheter, since the sheath would inhibit inflating of a balloon on the balloon catheter. Secondly, the sheath is unsuitable for use with a guide wire. For example, it is not possible to initially direct a guide wire to a remote site at which the procedure or investigation is to be carried out, and then subsequently pass the catheter along the guide wire, since the distal end of the sheath would have to be punctured to accommodate the guide wire through a guide wire accommodating lumen in the catheter. Thus bodily fluids and other bodily matter adhering to the guide wire would come into contact with the inner surface of the guide wire accommodating lumen of the catheter, thereby contaminating the catheter and thus rendering it unsuitable for reuse.

There is therefore a need for a method and a device for protecting a catheter during a procedure or investigation at a remote site in a human or animal body, so that the catheter can be reused on completion of the procedure or investigation. There is also a need for a method for facilitating use of such a protected catheter with a guide wire whereby the guide wire is initially used to access a remote site at which a procedure or investigation is to be carried out, which addresses at least some of the problems of prior art methods and devices.

The present invention is directed towards providing a method and a device for protecting a catheter, and the invention is also directed towards providing a method for locating a catheter at a remote site, for example, a remote site in a human or animal body, so that the catheter may be reused.

SUMMARY OF THE INVENTION

According to the invention there is provided a device for protecting a balloon catheter, the device comprising an elongated sheath extending between an open proximal end and a closed distal end, the proximal end of the sheath defining a proximal opening into the sheath, the sheath being adapted to accommodate the balloon catheter therein, and comprising a balloon accommodating portion adapted to accommodate a balloon of the balloon catheter, and being adapted to permit substantially unrestricted inflating of the balloon of the balloon catheter to a predefined maximum volume.

Preferably, the balloon accommodating portion is located to accommodate the balloon of the balloon catheter when the balloon catheter is fully located in the sheath.

In one embodiment of the invention the balloon accommodating portion is located adjacent the distal end of the sheath.

Preferably, the sheath is adapted to slideably accommodate the balloon catheter therein for accommodating the balloon of the balloon catheter into the balloon accommodating portion of the sheath.

Advantageously, the sheath is of a material configurable to adopt a transverse cross-section of shape substantially similar to the shape of the transverse cross-section of the balloon catheter. Ideally, the transverse cross-section of the sheath when adopting the shape substantially similar to the shape of the transverse cross-section of the balloon catheter is of transverse cross-section greater than the transverse cross-section of the balloon catheter.

In one embodiment of the invention the sheath is of a material configurable to define an elongated bore through which the balloon catheter is longitudinally slideable from the proximal opening to the distal end of the sheath.

Preferably, the sheath is of a flexible material.

Advantageously, the balloon accommodating portion is of a material configurable to adopt a transverse cross-section of shape substantially similar to the shape of the transverse cross-section adopted by the balloon of the balloon catheter when inflated.

In one embodiment of the invention the transverse cross-section of the balloon accommodating portion when adopting the shape substantially similar to the shape of the transverse cross-section of the balloon when inflated to the maximum predefined volume is of transverse cross-section which is equal to the transverse cross-section of the balloon when inflated to the predefined maximum volume. In an alternative embodiment of the invention the transverse cross-section of the balloon accommodating portion when adopting the shape substantially similar to the shape of the transverse cross-section of the balloon when inflated to the maximum predefined volume is of transverse cross-section which is greater than the transverse cross-section of the balloon when inflated to the predefined maximum volume.

Preferably, the balloon accommodating portion is urgeable by the balloon of the balloon catheter from a collapsed state with the balloon of the balloon catheter deflated to an erect state with the balloon of the balloon catheter inflated to the predefined maximum volume with substantially no stretching of the material of the balloon accommodating portion.

Advantageously, the balloon accommodating portion is adapted to be of greater transverse cross-sectional area when in the erect state than the transverse cross-sectional area of the sheath when configured to accommodate the transverse cross-section of the catheter of the balloon catheter.

In one embodiment of the invention the balloon accommodating portion is of material similar to the material of the sheath. Preferably, the sheath and the balloon accommodating portion of the sheath are integrally formed. Advantageously, the sheath is of a film material.

In one embodiment of the invention the film material of the sheath is of thickness in the range of 25 microns to 75 microns, and preferably, the film material of the sheath is of thickness of the order of 50 microns.

Ideally, the sheath is of a plastics material.

In one embodiment of the invention the balloon accommodating portion of the sheath is of axial length substantially similar to the axial length of the balloon of the balloon catheter. In an alternative embodiment of the invention the balloon accommodating portion of the sheath is of axial length greater than the axial length of the balloon of the balloon catheter.

In another embodiment of the invention the sheath is adapted to accommodate a guide wire.

In one embodiment of the invention the sheath is adapted to internally accommodate a guide wire. Preferably, the sheath is adapted to accommodate the guide wire through the proximal opening into the sheath with the distal end of the guide wire located adjacent the distal end of the sheath. Advantageously, the distal end of the sheath is adapted to engage the distal end of the guide wire. Ideally, the sheath comprises a locating means adjacent the distal end thereof for locating the distal end of the guide wire adjacent the distal end of the sheath.

In one embodiment of the invention the locating means comprises a distal portion of the sheath of transverse cross-sectional area adapted to engage the distal end of the guide wire. Preferably, the locating means is adapted to releasably engage the distal end of the guide wire. Advantageously, the locating means slideably engages the guide wire.

In an alternative embodiment of the invention the locating means is formed by a distal portion of the sheath, the distal portion of the sheath tapering to an apex engageable with the distal end of the guide wire.

In one embodiment of the invention the sheath is adapted to accommodate passing a balloon catheter through the sheath along a guide wire located in the sheath.

In an alternative embodiment of the invention the sheath is adapted to engage a guide wire externally of the sheath. Preferably, the sheath comprises an engagement means for engaging the guide wire externally of the sheath. Advantageously, the engagement means is adapted for slideably engaging the guide wire. Ideally, the engagement means is located externally of the sheath.

Preferably, the engagement means is connected to the sheath.

In one embodiment of the invention the engagement means comprises an engagement element having a guide wire accommodating opening extending therethrough. Preferably, the engagement element extends from the sheath. Advantageously, the engagement element extends transversely from the sheath. Ideally, the engagement element comprises a tab extending from the sheath.

Preferably, the guide wire accommodating opening is formed by a guide wire accommodating bore extending through the tab for slideably engaging the guide wire. Advantageously, the guide wire accommodating bore extending through the tab is defined by an eyelet located in the tab.

In another embodiment of the invention the engagement element comprises an elongated engagement element defining an elongated guide wire accommodating bore extending therethrough. Preferably, the engagement element is located on the sheath with the guide wire accommodating bore extending substantially parallel to the sheath. Advantageously, the engagement element is located extending along the balloon accommodating portion of the sheath.

Preferably, the engagement element is integrally formed with the sheath.

In one embodiment of the invention the engagement means is located towards the distal end of the sheath.

In another embodiment of the invention a plurality of engagement means are provided spaced apart along the sheath.

The invention also provides a combination of the sheath of the device according to the invention and a balloon catheter, and preferably, the combination of the sheath of the device according to the invention and the balloon catheter also comprises a guide wire.

The invention further provides a device for protecting a catheter, the device comprising an elongated sheath extending between an open proximal end and a closed distal end, the proximal end of the sheath defining a proximal opening to the sheath, the sheath being adapted to accommodate a guide wire and a catheter therein through the proximal opening, the distal end of the sheath being adapted to engage a distal end of a guide wire, and the sheath being adapted to accommodate passing a catheter through the sheath along a guide wire located in the sheath.

Preferably, the sheath comprises a locating means adjacent the distal end thereof for locating the distal end of the guide wire adjacent the distal end of the sheath. Advantageously, the locating means comprises a distal portion of the sheath of transverse cross-sectional area adapted to engage the distal end of the guide wire. Ideally, the transverse cross-sectional area of the locating means is adapted to snugly and slideably engage the distal end of the guide wire therein.

In one embodiment of the invention the locating means is formed of similar material to the material of the sheath. Preferably, the locating means is formed integrally with the sheath.

In one embodiment of the invention the locating means comprises a distal tapering portion of the sheath which substantially tapers to an apex at the distal end of the sheath for locating the distal end of the guide wire adjacent the distal end of the sheath.

In another embodiment of the invention the sheath is adapted to slideably accommodate the catheter through the sheath.

Preferably, the sheath is of a material configurable to adopt a transverse cross-section of shape substantially similar to the shape of the transverse cross-section of the catheter.

The invention also provides a combination of the device according to the invention and a catheter, and preferably, the combination of the device according to the invention and the catheter also comprises a guide wire.

Further the invention provides a device for protecting a catheter, the device comprising an elongated sheath extending between an open proximal end and a closed distal end, the proximal end of the sheath defining a proximal opening to the sheath, the sheath being adapted to accommodate the catheter therein through the proximal opening, and an engagement means being connected to the sheath for engaging a guide wire externally of the sheath.

In one embodiment of the invention the engagement means is located adjacent the distal end of the sheath.

In another embodiment of the invention the engagement means is of a material similar to the material of the sheath. Preferably, the engagement means is formed integrally with the sheath.

In one embodiment of the invention a plurality of engagement means are provided spaced apart along the sheath.

The invention also provides an engagement element for a sheath for a catheter, the engagement element being adapted for mounting externally on the sheath and having a guide wire accommodating opening for slideably engaging a guide wire.

The invention further provides a method for protecting a catheter, the method comprising providing an elongated sheath extending between an open proximal end and a closed distal end, the proximal end of the sheath defining a proximal opening into the sheath, the sheath being adapted to accommodate the catheter therein through the proximal opening, the method further comprising passing a guide wire into the sheath through the proximal opening thereof, and passing the catheter into the sheath through the proximal opening thereof over the guide wire.

In one embodiment of the invention the guide wire is located in the sheath with a distal end of the guide wire adjacent the distal end of the sheath. Preferably, the distal end of the sheath is adapted to engage the distal end of the guide wire.

In one embodiment of the invention the sheath is adapted for protecting a balloon catheter, and the sheath is provided with a balloon accommodating portion for accommodating a balloon of the balloon catheter, and the catheter is passed along the guide wire through the sheath until the balloon of the balloon catheter is located in the balloon accommodating portion of the sheath. Preferably, the balloon accommodating portion is located to accommodate the balloon of the balloon catheter when the balloon catheter is fully located in the sheath.

Additionally, the invention provides a method for locating a catheter at a remote site in a human or animal body, the method comprising providing an elongated sheath extending between an open proximal end and a closed distal end, the proximal end defining a proximal opening into the sheath, the sheath being adapted to accommodate the catheter through the proximal opening, the method further comprising passing a guide wire into the sheath through the proximal opening thereof, urging the guide wire sheathed by the sheath through a lumen, vessel or vascular system in the human or animal body until a distal end of the sheathed guide wire is located substantially adjacent the remote site, passing the catheter into the sheath through the proximal opening along the guide wire with a lumen of the catheter engaging the guide wire until a distal end of the catheter is located adjacent the remote site.

In one embodiment of the invention the guide wire is passed through the sheath until the distal end of the guide wire engages the distal end of the sheath.

In another embodiment of the invention the catheter is passed through the sheath until the distal end of the catheter is located adjacent the distal end of the sheath.

Preferably, the distal end of the sheath is adapted to engage the distal end of the guide wire.

Advantageously, the lumen of the catheter adjacent the distal end thereof is engaged on a proximal end of the guide wire prior to passing the catheter into the sheath.

In one embodiment of the invention the balloon accommodating portion is adapted to permit substantially unrestricted inflating of the balloon of the balloon catheter to a predefined maximum volume. Preferably, the balloon accommodating portion is of a material configurable to adopt a transverse cross-section of shape substantially similar to the shape of the transverse cross-section of the balloon of the balloon catheter when inflated.

In one embodiment of the invention the transverse cross-section of the balloon accommodating portion when adopting the shape substantially similar to the shape of the transverse cross-section of the balloon when inflated to the maximum predefined volume is of transverse cross-section which is equal to the transverse cross-section of the balloon when inflated to the predefined maximum volume. In an alternative embodiment of the invention the transverse cross-section of the balloon accommodating portion when adopting the shape substantially similar to the shape of the transverse cross-section of the balloon when inflated to the maximum predefined volume is of transverse cross-section which is greater than the transverse cross-section of the balloon when inflated to the predefined maximum volume.

The invention also provides a method for locating a catheter at a remote site of a human or animal body, the method comprising providing an elongated sheath extending between an open proximal end and a closed distal end, the proximal end of the sheath defining a proximal opening into the sheath, the sheath being adapted to accommodate the catheter therein through the proximal opening, providing an engagement means on the sheath for engaging a guide wire externally of the sheath, the method further comprising urging the catheter into the sheath through the proximal opening until the distal end of the catheter is located adjacent the distal end of the sheath with the catheter sheathed by the sheath, urging a guide wire through a lumen, vessel or a vascular system in the human or animal body until a distal end of the guide wire is substantially adjacent the remote site, and urging the sheathed catheter through the lumen or the vascular system along the guide wire with the engagement means slideably engaging the guide wire until a distal end of the sheathed catheter is located adjacent the remote site.

In one embodiment of the invention the catheter to be located at the remote site is a balloon catheter and the sheath is provided with a balloon accommodating portion for accommodating a balloon of the balloon catheter, and the catheter is passed through the sheath until the balloon of the balloon catheter is located in the balloon accommodating portion of the balloon catheter with the balloon catheter sheathed by the sheath.

Preferably, the balloon accommodating portion is located to accommodate the balloon of the balloon catheter when the balloon catheter is fully located in the sheath. Advantageously, the balloon accommodating portion is located adjacent the distal end of the sheath.

The advantages of the device according to the invention are many. The sheath of the devices protects the catheter or balloon catheter from contamination by bodily fluids and other bodily matter during use of the catheter or balloon catheter in carrying out a procedure or an investigation at a remote site in the human or animal body. This, thus, permits the balloon catheter to be reused many times. Additionally, where the sheath of the devices according to the invention are adapted to also accommodate a guide wire within the sheath, the guide wire is also protected from contamination by bodily fluids and other bodily matter during use of the catheter or balloon catheter in carrying out a procedure or investigation at a remote site in a human or animal body, and thus, the guide wire can likewise be reused. Additionally, the sheaths of the devices according to the invention can be readily easily removed from the catheter or balloon catheter without danger of bodily fluids or other bodily matter which may adhere to the sheath contaminating the catheter or balloon catheter.

A further advantage of the invention is achieved when the sheaths are provided with an engagement means for externally engaging a guide wire, in that the sheath is suitable for use with a catheter or balloon catheter of the type which is unsuitable for guiding along a guide wire with the guide wire extending through a guide wire accommodating lumen within the catheter or balloon catheter, since the external guide wire engagement means provided externally on the sheath facilitates engagement with a guide wire externally of the sheath, and in turn externally of the catheter or balloon catheter.

BRIEF DESCRIPTION OF THE DRAWINGS

The invention will be more clearly understood from the following description of some preferred embodiments thereof, which are given by way of example only, with reference to the accompanying drawings, in which.

DETAILED DESCRIPTION OF THE INVENTION

Figure 1:
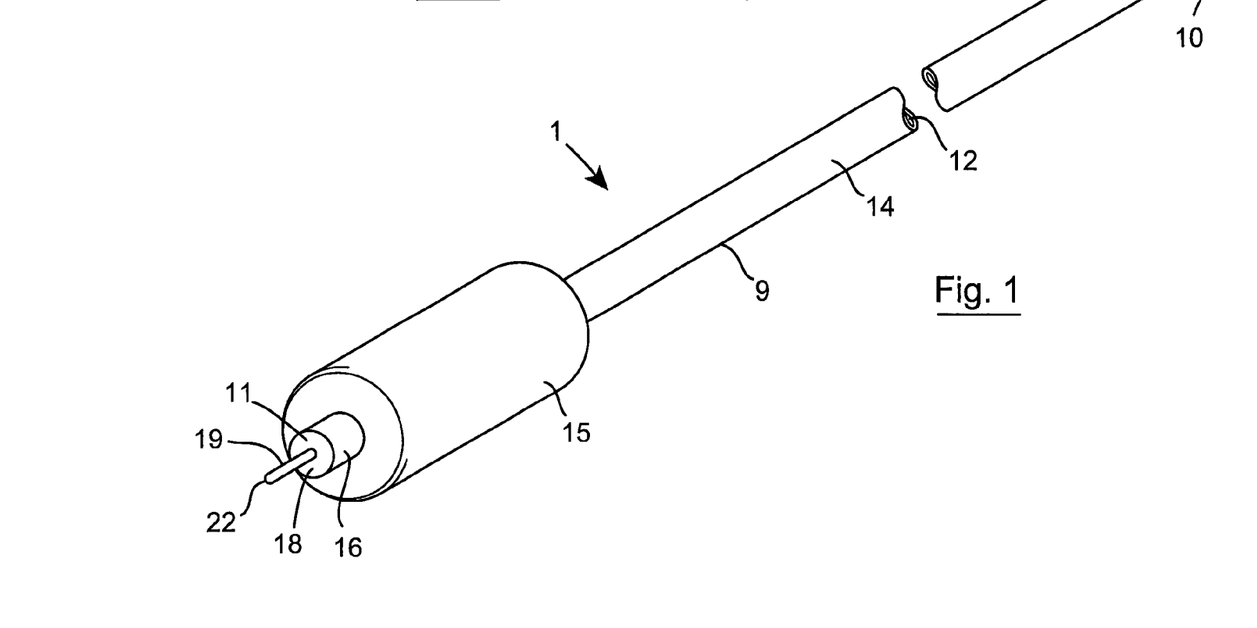
FIG. 1 is a perspective view of a device according to the invention for protecting a balloon catheter.
Figure 2:
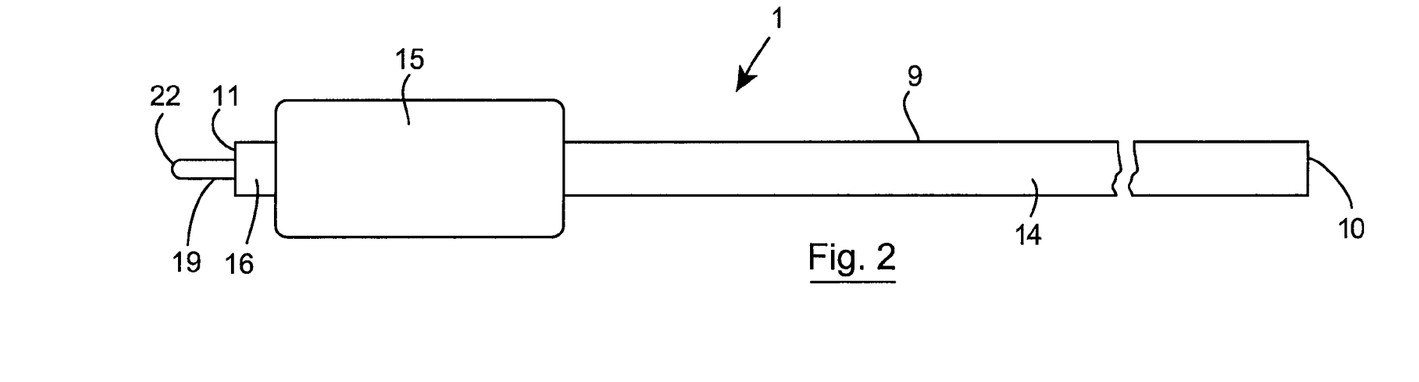
FIG. 2 is a side elevational view of the device of FIG. 1.
Figure 3:
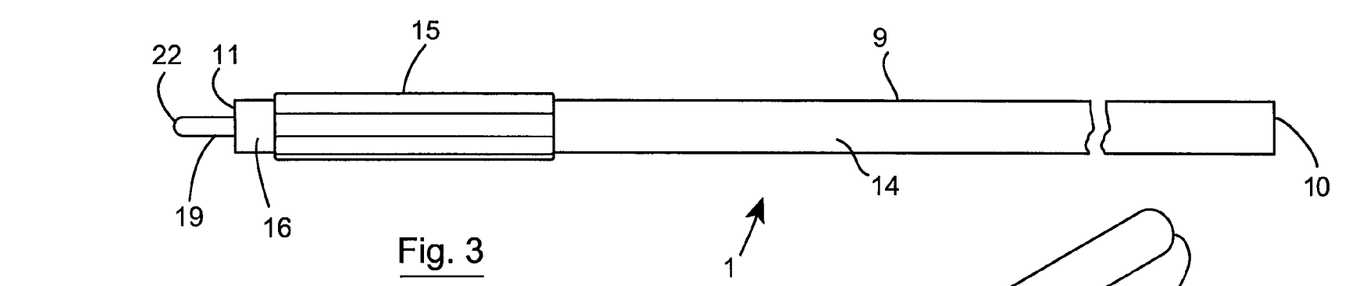
FIG. 3 is another side elevational view of the device of FIG. 1 in a different state to that of FIG. 2.
Figure 4:
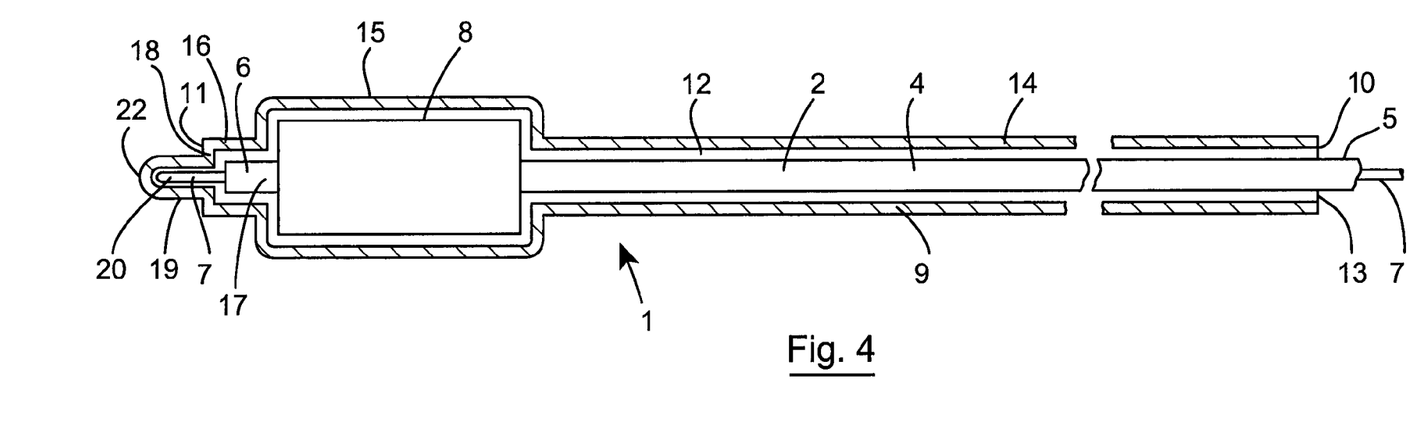
FIG. 4 is a cross-sectional side elevational view of the device of FIG. 1 in use.
Figures 5, 6:
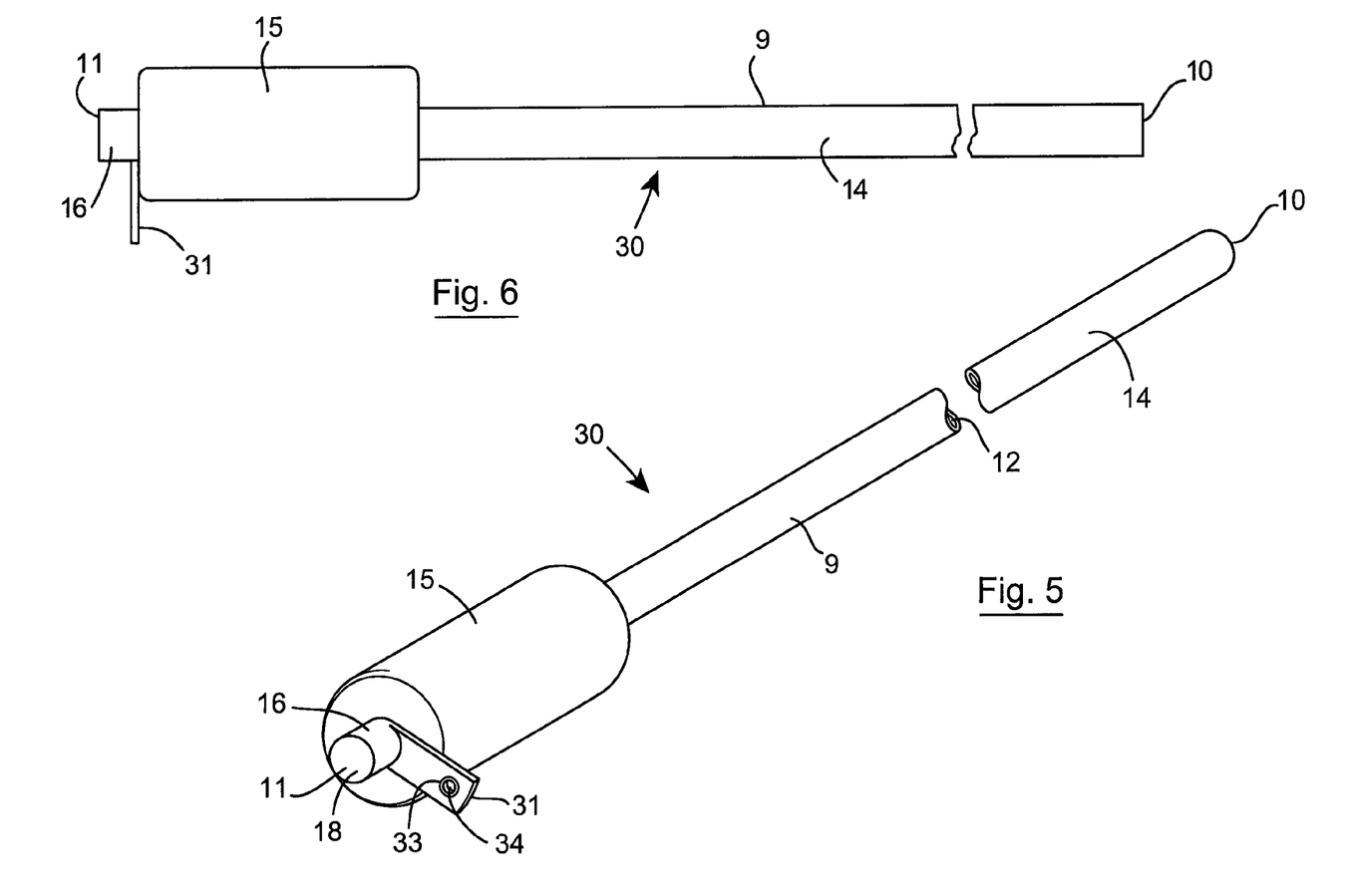
FIG. 5 is a perspective view of a device according to another embodiment of the invention for protecting a balloon catheter.
FIG. 6 is a top plan view of the device of FIG. 5.
Figure 7:
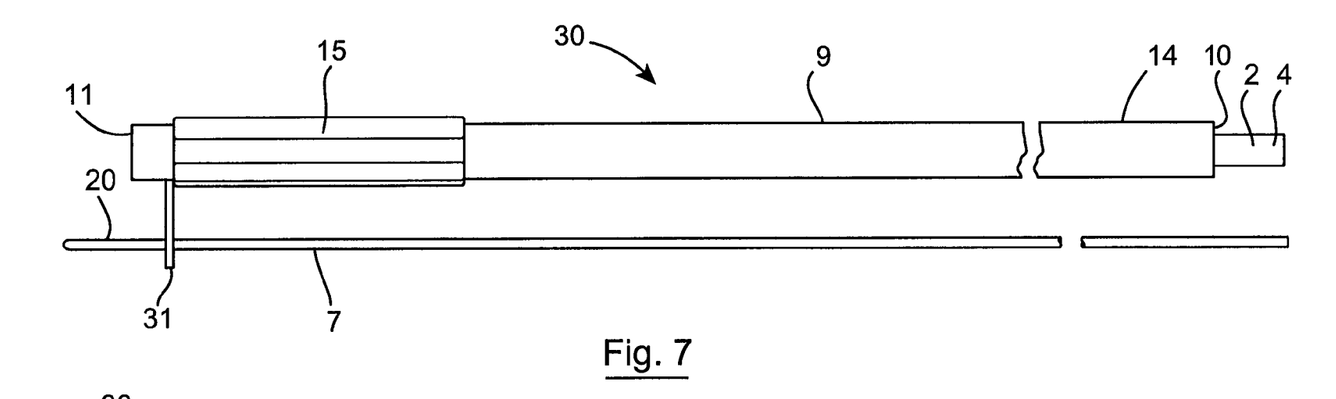
FIG. 7 is a top plan view of the device of FIG. 5 illustrating the device in use.
Figure 8:
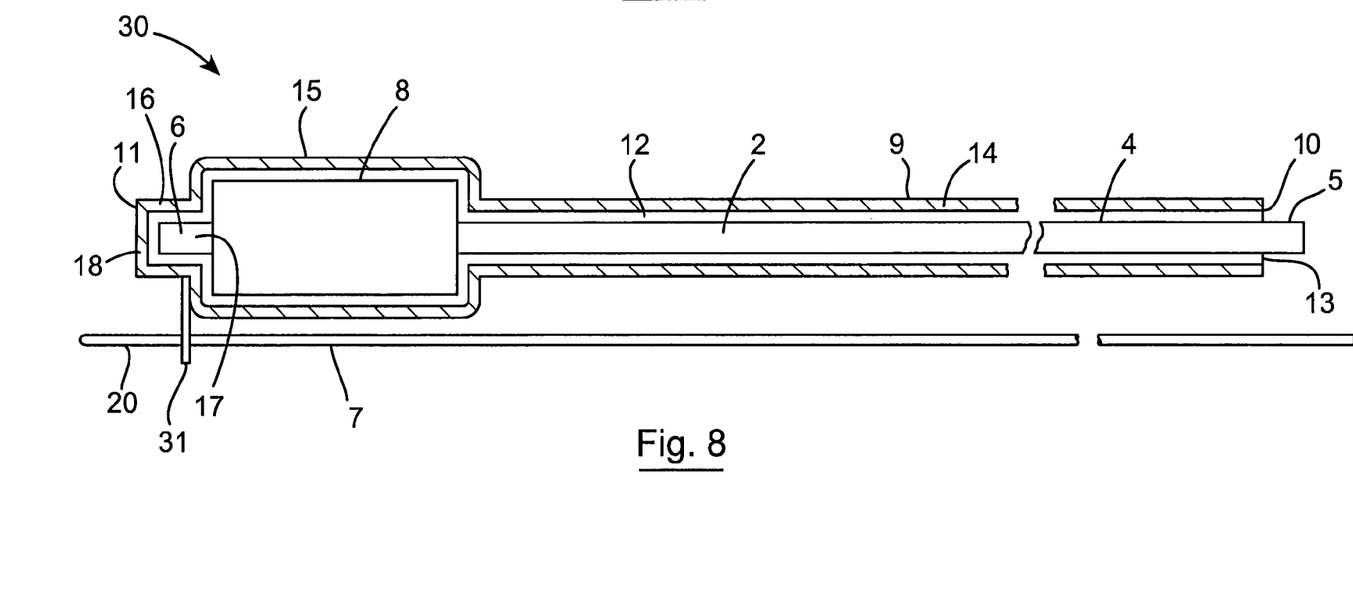
FIG. 8 is a transverse cross-sectional top plan view of the device of FIG. 5 also in use.

Referring to the drawings and initially to FIGS. 1 to 4 thereof, there is illustrated a device according to the invention, indicated generally by the reference numeral 1, for protecting a balloon catheter 2 from contamination by bodily fluids and other bodily matter during use in carrying out a procedure or an investigation at a remote site in a human or animal body, so that the balloon catheter 2 can be reused on completion of the procedure or investigation. Before describing the device 1 in detail, the balloon catheter 2 will first be described. Referring in particular to FIG. 4, the balloon catheter 2 may be any type of balloon catheter, and in this case comprises an elongated catheter 4 of circular transverse cross-section extending from a proximal end 5 to a distal end 6, and having a guide wire accommodating lumen (not shown) extending therethrough from the proximal end 5 to the distal end 6 for accommodating a guide wire 7 therethrough. A balloon 8, which when inflated is of circular transverse cross-section, is located on the catheter 4 adjacent the distal end 6, and the catheter 4 extends through the balloon 8 and defines with the balloon 8 when inflated a hollow annular interior region (not shown).

A plurality of longitudinally spaced apart band electrodes (also not shown) are located on the catheter 4 within the hollow interior region of the balloon 8. Two of the electrodes which are the outermost electrodes are stimulating electrodes, and the electrodes located between the stimulating electrodes are sensing electrodes. When the balloon 8 is inflated with an electrically conductive medium, for example, a saline solution, by applying an electrical constant current signal of known current value through the two outermost stimulating electrodes, and reading voltage signals produced on the sensing electrodes, values of the transverse cross-sectional area or diameter of the balloon 8 at locations corresponding to the electrodes may be determined. Additionally, by knowing the spacing between the sensing electrodes, the volume of the balloon 8 between any two sensing electrodes may then also be determined.

Such balloon catheters 2 are typically provided for determining the transverse cross-sectional area and the distensibility of a sphincter at a remote site in the human or animal body with the balloon 8 located in the sphincter, and such balloon catheters 2 are also provided for determining the transverse cross-sectional area, the volume and the distensibility of a lumen or vessel or a part thereof at a remote site in the human or animal body within which the balloon 8 is located.

A typical example of such a balloon catheter as the balloon catheter 2 is disclosed in PCT Published Application Specifications Nos. WO 2009/001325 and WO 2009/001328. However, it will be readily apparent to those skilled in the art that the device 1 according to the invention may be used for protecting any type of balloon catheter, irrespective of the purpose for which the balloon catheter is provided.

The device 1 comprises an elongated sheath 9 of flexible plastics film material, in this embodiment of the invention polyurethane film material of film thickness of the order of 50 microns. The sheath 9 extends from an open proximal end 10 to a distal end 11 and defines a hollow interior region 12 for accommodating the balloon catheter therein. The proximal end 10 of the sheath 9 defines a proximal opening 13 to the hollow interior region 12. The sheath 9 defines a catheter accommodating portion 14 extending from the proximal opening 13 for accommodating the catheter 4 of the balloon catheter 2, and a balloon accommodating portion 15 adjacent the distal end 11 of the sheath 9 for accommodating the balloon 8 of the balloon catheter 2. The balloon accommodating portion 15 and the catheter accommodating portion 14 are integrally formed of the same polyurethane film material of film thickness of the order of 50 microns.

Since the sheath 9 is of flexible polyurethane film material of 50 microns thickness, the sheath 9 is not self-supporting, and when not accommodating the balloon catheter 2, the sheath will not take up any particular transverse cross-section, but rather will lie relatively flat on a surface on which it is supported. However, being of such flexible film material, the catheter accommodating portion 14 of the sheath 9 is configurable to take up any suitable transverse cross-section, as is the proximal opening 13 to accommodate the transverse cross-section of a catheter of a balloon catheter which is located in the hollow interior region 12 of the sheath 9. Similarly, the balloon accommodating portion 15 is configurable to take up any suitable transverse cross-section to accommodate the transverse cross-section of an inflated balloon of a balloon catheter located within the hollow interior region 12. Thus, when accommodating a balloon catheter, such as the balloon catheter 2, the catheter 4, and the balloon 8 of which are of circular transverse cross-section, the catheter accommodating portion 14 takes up a transverse cross-section of shape which is substantially similar to the circular transverse cross-section of the catheter 4, and the proximal opening 13 takes up a transverse cross-section of shape which is substantially similar to the circular transverse cross-section of the catheter 4. Similarly, the balloon accommodating portion 15 takes up a transverse cross-section to of shape which is substantially similar to the circular transverse cross-section of the balloon 8 when inflated, or any other transverse cross-section which the balloon 8 takes up when inflated in order to fill a vessel, lumen or sphincter.

However, in order to accommodate the balloon 8 when deflated and the catheter 4 of the balloon catheter 2 through the catheter accommodating portion 14 of the sheath 9, the circumferential length of the material of the catheter accommodating portion 14 of the sheath 9 is such that when the shape of the transverse cross-section of the catheter accommodating portion 14 is substantially similar to the shape of the transverse cross-section of the catheter 4, the transverse cross-sectional area of the catheter accommodating portion 14 is greater than the transverse cross-sectional area of the catheter 4 and is also greater than the transverse cross-sectional area of the balloon 8 when deflated, in order to accommodate slideable movement of the balloon catheter 2 through the catheter accommodating portion 14 of the sheath 9. The circumferential length of the film material forming the balloon accommodating portion 15 of the sheath 9 is of sufficient length to accommodate substantially unimpeded inflating of the balloon 8 of the balloon catheter 2 to a predefined maximum volume. In other words, the balloon accommodating portion 15 can be erected by inflating the balloon 8 to any volume without stretching or tensioning the film material of the balloon accommodating portion 15 up to a volume corresponding to the predefined maximum volume of the balloon 8. The predefined maximum volume may be any desired volume and will be dependent on the procedure or investigation to be carried out with the balloon catheter 2. However, in order to accommodate inflating of the balloon 8 to the predefined maximum volume without stretching or tensioning the film material of the balloon accommodating portion 15, the transverse cross-sectional area of the balloon accommodating portion 15 when the balloon 8 is inflated to the predefined maximum volume, in general, would be slightly greater than the transverse cross-sectional area of the balloon 8 when inflated to the predefined maximum volume. Additionally, in order to accommodate inflating of the balloon to the predefined maximum volume without stretching or tensioning the film material of the balloon accommodating portion 15, in general, the axial length of the balloon accommodating portion 15 will be somewhat greater than the axial length of the balloon 8.

Thus, it is envisaged that a range of sheaths 9 of different sizes will be provided to accommodate balloon catheters of different sizes and shapes, and in particular, to accommodate balloons of transverse cross-section when inflated of different sizes and shapes, and balloons of different axial lengths, as well as to accommodate catheters of transverse cross-section of different sizes and shapes, as well as catheters of different lengths.

When the balloon 8 of the balloon catheter 2 is in a deflated state within the balloon accommodating portion 15, the balloon accommodating portion 15 may be folded to a collapsed state around the deflated balloon 8 so that the balloon accommodating portion 15 is of substantially similar transverse cross-section to that of the catheter accommodating portion 14, see FIG. 3, for facilitating urging of the sheathed catheter through a lumen, vessel or a vascular system to the remote site. When the balloon 8 of the balloon catheter 2 is inflated to the predefined maximum volume, the balloon accommodating portion 15 is supported in an erect state by the balloon 8, and is of substantially similar transverse cross-section to that of the transverse cross-section of the inflated balloon 8.

As discussed above, the internal transverse cross-sectional area of the catheter accommodating portion 14 and the proximal opening 13 is such as to slideably accommodate the balloon catheter 2 with the balloon 8 in a deflated state through the catheter accommodating portion 14 until the balloon 8 is located in the balloon accommodating portion 15.

A distal portion 16 of the catheter accommodating portion 14 of the sheath 9 extends from the balloon accommodating portion 15 for protecting a corresponding distal portion 17 of the catheter 4 of the balloon catheter 2. An end wall 18 closes the distal portion 16, and in turn the sheath 9.

A locating means, in this embodiment of the invention a guide wire engaging distal portion 19 of the sheath 9 extends centrally and axially from the end wall 18 at the closed distal end 11 of the sheath 9 and communicates with the hollow interior region 12 of the sheath 9 through the end wall 18 for accommodating a distal end 20 of the guide wire 7 extending through the guide wire accommodating lumen (not shown) in the balloon catheter 2. The guide wire engaging distal portion 19 is also closed at its distal end 22 in order to maintain the distal end 12 of the sheath 9 closed. The internal diameter of the guide wire engaging distal portion 19 of the sheath 9 is substantially similar to the outer diameter of the distal end 20 of the guide wire 7 for releasably and snugly and slideably engaging the distal end 20 of the guide wire 7 therein. Typically, the diameter of the guide wire engaging distal portion 19 is of diameter just greater than that of the distal end 20 of the guide wire 7, so that the distal end 20 of the guide wire 7 can be easily engaged and removed from the guide wire engaging distal portion 19.

In use, to carry out a procedure or investigation at a remote site in a human or animal body with a catheter, such as the balloon catheter 2 with the balloon catheter 2 protected by the sheath 9, initially a guide wire, such as the guide wire 7 is passed into the sheath 9 through the proximal opening 13 and through the hollow interior region 12 until the distal end 20 of the guide wire 7 extends into the guide wire engaging distal portion 19, and is snugly engaged therein. The guide wire 7 thus sheathed with the sheath 9 is then urged through the appropriate lumen, vessel or a venal, arterial or other vascular system of the human or animal body until the distal end 20 of the sheathed guide wire 7 is located adjacent the remote site in the human or animal body at which the procedure or investigation is to be carried out. With the sheathed guide wire 7 located at the remote site in the human or animal body, the distal end 6 of the guide wire accommodating lumen (not shown) of the balloon catheter 2 is engaged on the proximal end of the guide wire 7, and the balloon catheter 2 is then passed along the guide wire 7, and in turn is entered into the hollow interior region 12 of the sheath 9 through the proximal opening 13. The balloon catheter 2 is urged along the guide wire 7 through the sheath 9 until the distal end portion 17 of the balloon catheter 2 is located within the distal end portion 16 of the sheath 9 and the balloon 8 of the balloon catheter 2 aligned with and located within the balloon accommodating portion 15 of the sheath 9. At this stage the balloon 8 of the sheathed balloon catheter 2 is located in and aligned with the remote site.

The balloon 8 of the balloon catheter 2 is then inflated, and due to the size and flexibility of the material of the balloon accommodating portion 15, inflation of the balloon 8 is carried out unimpeded by the balloon accommodating portion 15 until the balloon 8 is inflated to the predefined maximum volume. However, it is desirable that the balloon 8 should not be inflated beyond the maximum predefined volume, otherwise inflating of the balloon 8 would be impeded by the balloon accommodating portion 15. Any impeding of inflating of the balloon 8 would lead to spurious results if an investigation being carried out at the remote site relied on a relationship between volume or transverse cross-sectional area of the balloon 8 and inflating pressure of the inflating medium.

Prior to inflating of the balloon 8 of the balloon catheter 2, if desired the guide wire 7 may be withdrawn.

On completion of the procedure or investigation, the sheathed balloon catheter 2 is withdrawn from the human or animal body, and if the guide wire 7 had not already been withdrawn from the balloon catheter 2 prior to inflating of the balloon 8, the guide wire is withdrawn either prior to or simultaneously with the withdrawal of the sheathed balloon catheter 2 from the subject.

It should, however, be noted that the balloon catheter 2 and the sheath 9 should be simultaneously withdrawn from the subject.

On being withdrawn from the subject, the sheath 9 is then carefully removed from the balloon catheter 2 in order to avoid any danger of bodily fluids and other bodily matter which may adhere to the sheath 9 contaminating the balloon catheter 2. With the sheath 9 having been carefully removed from the balloon catheter 2, the balloon catheter 2 is clean and should be ready for reuse. However, for safety, in general the balloon catheter 2 would be wiped with an alcohol wipe. Additionally, since the guide wire 7 is also protected by the sheath 9, the guide wire 7 is also ready for reuse after being wiped with an alcohol wipe.

While the device 1 has been described for use with a guide wire, it is envisaged that the device 1 may be used without a guide wire, in which case the balloon catheter 2 would be sheathed with the sheath 9 so that the balloon of the balloon catheter is located in the balloon accommodating portion 15 of the sheath 9, and the sheathed balloon catheter 2 would then be urged through an appropriate vessel, lumen or vascular system to the remote site. It is envisaged that the device 1 could be used without a catheter, when the sheath 9 is adapted for use with a balloon catheter suitable for carrying out a procedure in the oesophagus, oesophageal sphincter, stomach, where the sheathed balloon catheter would be entered nasally or orally into the subject. It is also envisaged that where the sheath of the device 1 is adapted for sheathing a balloon catheter suitable for carrying out a procedure or investigation in the bowel, the large intestine or the small intestine, it is envisaged that the sheathed catheter sheathed with the sheath of the device 1 may be used without a guide wire, and in which case, the sheathed balloon catheter would be entered rectally into the subject.

Referring now to FIGS. 5 to 8, there is illustrated a device, indicated generally by the reference numeral 30, according to another embodiment of the invention, for protecting a balloon catheter, which is similar to the balloon catheter 2, and is also identified by the reference numeral 2. The components of the balloon catheter 2 of FIGS. 5 to 8 are identified by the same reference numerals as the corresponding components of the balloon catheter 2 of FIGS. 1 to 4. The device 30 is substantially similar to the device 1, and similar components are identified by the same reference numerals. The main difference between the device 30 and the device 1 is that the guide wire engaging distal portion which was provided at the distal end of the sheath 9 of the device 1 has been omitted in the device 30.

However, in order to accommodate guiding of the balloon catheter 2 when located within the sheath 9 through a lumen, a vessel or a vascular system of the human or animal body to a remote site therein along a guide wire such as the guide wire 7, when the guide wire 7 must be located externally of the balloon catheter 2, the sheath 9 of the device 30 is provided with a guide wire engaging means, namely, an engagement element which is also according to the invention, and in this case comprises a tab 31 extending radially from the distal portion 16 of the sheath 9 adjacent the balloon accommodating portion 15. An eyelet 33 located in the tab 31 defines a guide wire engaging bore 34 for slideably engaging a guide wire 7, so that the balloon catheter 2 within the sheath 9 can be guided along the guide wire 7 through the lumen, vessel or vascular system of a human or animal subject. The tab 31 is of a material similar to that of the sheath 9, and is ultrasonically welded to the sheath 9 adjacent the balloon accommodating portion 15.

Otherwise the device 30 is similar to the device 1.

In use, the balloon catheter 2 located within and sheathed by the sheath 9, with the balloon 8 located in the balloon accommodating portion 15 is guided to the remote site in the human or animal body through the lumen, vessel or vascular system, as the case may be along the guide wire 7. The guide wire 7 is initially passed through the lumen, vessel or vascular system until the distal end 20 of the guide wire 7 is located adjacent the remote site. With the balloon catheter 2 located within the sheath 9, in other words, fully sheathed by the sheath 9, the eyelet 33 of the tab 31 is then engaged onto the guide wire 7 at the proximal end thereof. The sheathed balloon catheter 2 is urged along the guide wire 7 with the eyelet 33 slideably engaging the guide wire 7, thus guiding the sheathed balloon catheter 2 to the remote site through the lumen, vessel or vascular system of the human or animal body. On the balloon 8 of the sheathed balloon catheter 2 being located at the remote site, in general, the guide wire 7 is withdrawn, and the balloon 8 of the balloon catheter 1 is then inflated as already described.

Thereafter operation of the balloon catheter 2 and the device 30 is similar to that of the balloon catheter 2 and the device 1.

On completion of the procedure or investigation, the sheathed balloon catheter 2 is removed from the human or animal body, and the sheath 9 is then carefully removed from the balloon catheter 2 in order to avoid contamination of the balloon catheter 2 with bodily fluid and other bodily matter which may adhere to the sheath 9. Thereafter, the balloon catheter 2 is ready for use subject to being wiped with an alcohol wipe.

In this embodiment of the invention the guide wire 7 will most likely have become contaminated with bodily fluid and other bodily matter, and if the guide wire is being reused, thorough cleansing and sterilising of the guide wire would be required. However, if desired, the guide wire may also be sheathed with a sheath extending between an open proximal end and a closed distal end. The guide wire 21 located within the sheath would then be passed through the lumen, vessel or vascular system of the human or animal subject until the distal end of the sheathed guide wire is located adjacent the remote site. The eyelet 33 of the tab 31 would then be passed along the sheathed guide wire and urged along the sheathed guide wire for guiding the sheathed balloon catheter 2 to the remote site. On withdrawal of the sheathed guide wire from the subject, the sheath would then be carefully removed from the guide wire to avoid contamination of the guide wire with bodily fluids and other bodily matter which may adhere to the sheath.

Figure 9:
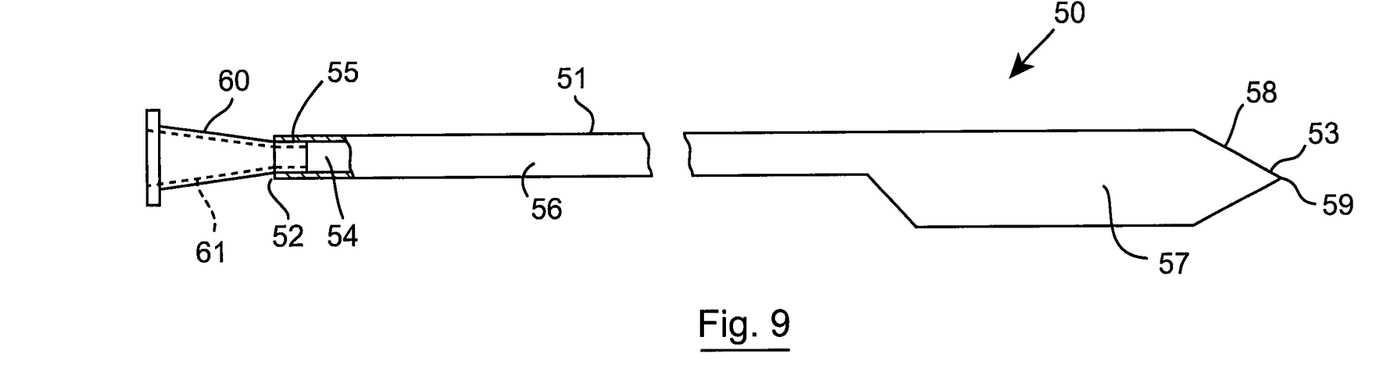
FIG. 9 is a top plan view of a device according to another embodiment of the invention for protecting a balloon catheter.
Figure 10:
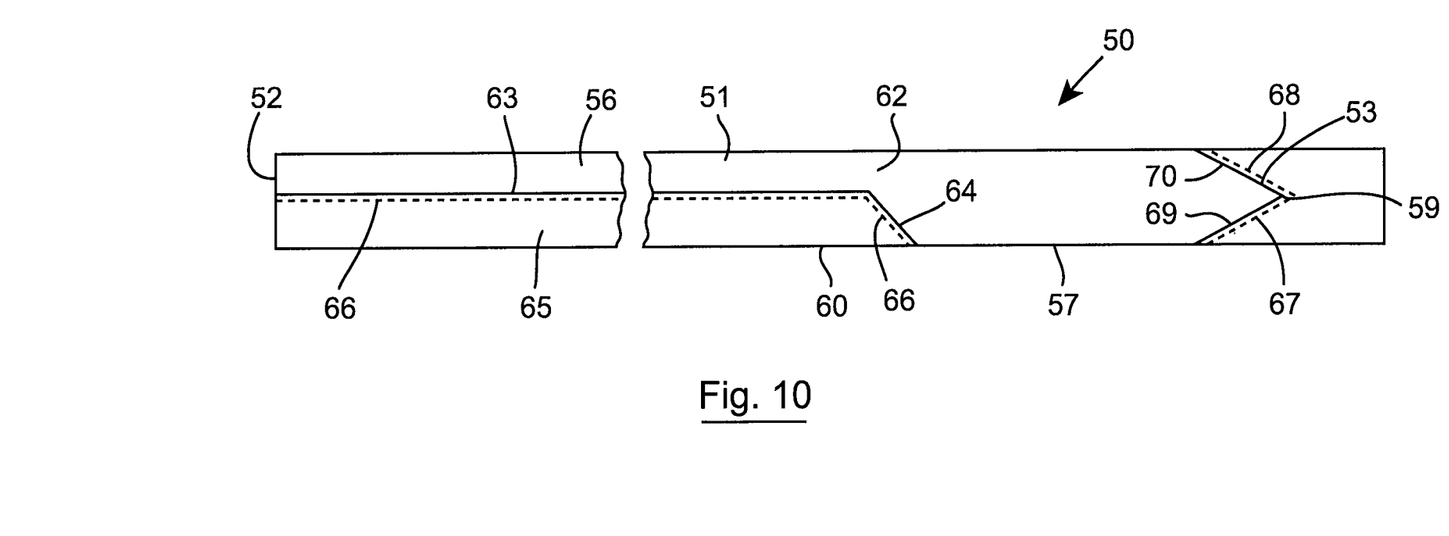
FIG. 10 is a top plan view of the device of FIG. 9 in a state of being manufactured.

Referring now to FIGS. 9 and 10, there is illustrated a device according to another embodiment of the invention, indicated generally by the reference numeral 50, for protecting a balloon catheter, similar to the balloon catheter described with reference to FIGS. 1 to 4 from contamination by bodily fluids and other bodily matter during use, so that the balloon catheter may be reused. In this embodiment of the invention the device 50 comprises an elongated sheath 51 extending from an open proximal end 52 to a closed distal end 53, and defines a hollow interior region 54 for accommodating a balloon catheter similar to the balloon catheter 2 therein. A proximal opening 55 at the open proximal end 52 accommodates the balloon catheter into the hollow interior region 54.

The sheath 50 is formed in one piece as will be described below of either translucent or transparent polyurethane material of thickness of the order of 50 microns. The sheath 51 defines a catheter accommodating portion 56 extending from the proximal opening 55 and a balloon accommodating portion 57 adjacent the distal end 53 of the sheath 51. A distal portion 58 of the sheath 51 extends from the balloon accommodating portion 57 for accommodating the distal portion 17 of the catheter 2 and to form a locating means for locating a distal end of a guide wire such as the distal end 20 of the guide wire 7 in the sheath 51. The distal portion 58 converges to an apex 59 which acts as a locating means for locating the distal end 20 of the guide wire 7 centrally in the sheath 51.

An inlet hub 60 of plastics material is located in the proximal opening 55 and is sealably secured to the sheath 51 by heat welding of the sheath 51 to the inlet hub 60. A bore 61 through the inlet hub 60 communicates with the hollow interior region 54 of the sheath 51 for accommodating the guide wire 7 and the balloon catheter 2 into the hollow interior region 54 of the sheath 51.

Referring now in particular to FIG. 10, in this embodiment of the invention the device 50 is formed from an elongated tube 62 of polyurethane film material of approximately 50 microns thickness. The diameter of the tube 62 when configured to be of circular transverse cross-section is selected to correspond to the desired diameter of the balloon accommodating portion 57. The sheath 51 is formed from the elongated tube 62 by sealably securing opposite sides of the tube along a heat seal weld line 63 from the open proximal end 52 to the balloon accommodating portion 57. The heat seal weld line 63 inclines from the distal end of the catheter accommodating portion 56 to the balloon accommodating portion 57 at 64. A redundant portion 65 of the tube 62 is removed along the catheter accommodating portion 56 by cutting the redundant portion 65 from the remainder of the sheath along a cut line 66.

The distal end of the elongated tube 62 is cut with two bias cuts along cut lines 67 and 68, and the tube 62 is sealed along heat weld lines 69 and 70 in order to sealably close the distal end portion 58, and so that the distal end portion 58 converges to the apex 59, and the hollow interior region 54 is sealably closed.

In use, a guide wire such as the guide wire 7 is inserted into the hollow interior region 54 of the sheath 51 through the bore 61 of the inlet hub 60 at the open proximal end 52 until the distal end 20 of the guide wire engages within the apex 59 of the converging distal end portion 58. The sheathed guide wire 7 is then entered into the lumen, vessel or vascular system of the human or animal body and is urged therethrough until the distal end 20 of the sheathed guide wire 7 is located adjacent the remote site. With the distal end guide wire accommodating lumen of a balloon catheter such as the balloon catheter 2 engaged on the proximal end of the guide wire 7, the balloon catheter 2 is then passed along the guide wire 7 as already described with reference to the device 1 of FIGS. 1 to 4, and is entered through the bore 61 in the inlet hub 60 to the hollow interior region 54 of the sheath 51 until the balloon 8 of the balloon catheter 2 is located in the balloon accommodating portion 57. At which stage the balloon 8 of the balloon catheter and the balloon accommodating portion 57 should be located in and aligned with the remote site.

Thereafter use of the device 50 is similar to that of the device 1 described with reference to FIGS. 1 to 4.

While in this embodiment of the invention the balloon accommodating portion 57 of the device 50 is not axially aligned with the catheter accommodating portion 56 of the sheath 51, this does not affect the operation of the device 50. However, if desired, the device 50 could be appropriately formed from the elongated tube 62 with the balloon accommodating portion 57 substantially axially aligned with the catheter accommodating portion 56 as in the case of the devices 1 and 30.

Figure 11:
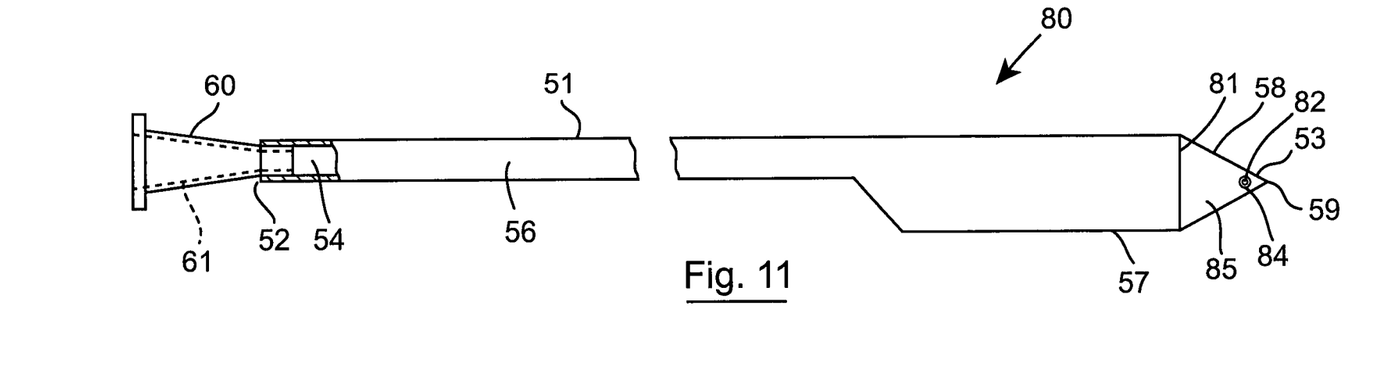
FIG. 11 is a top plan view of a device according to another embodiment of the invention for protecting a balloon catheter.
Figure 12:
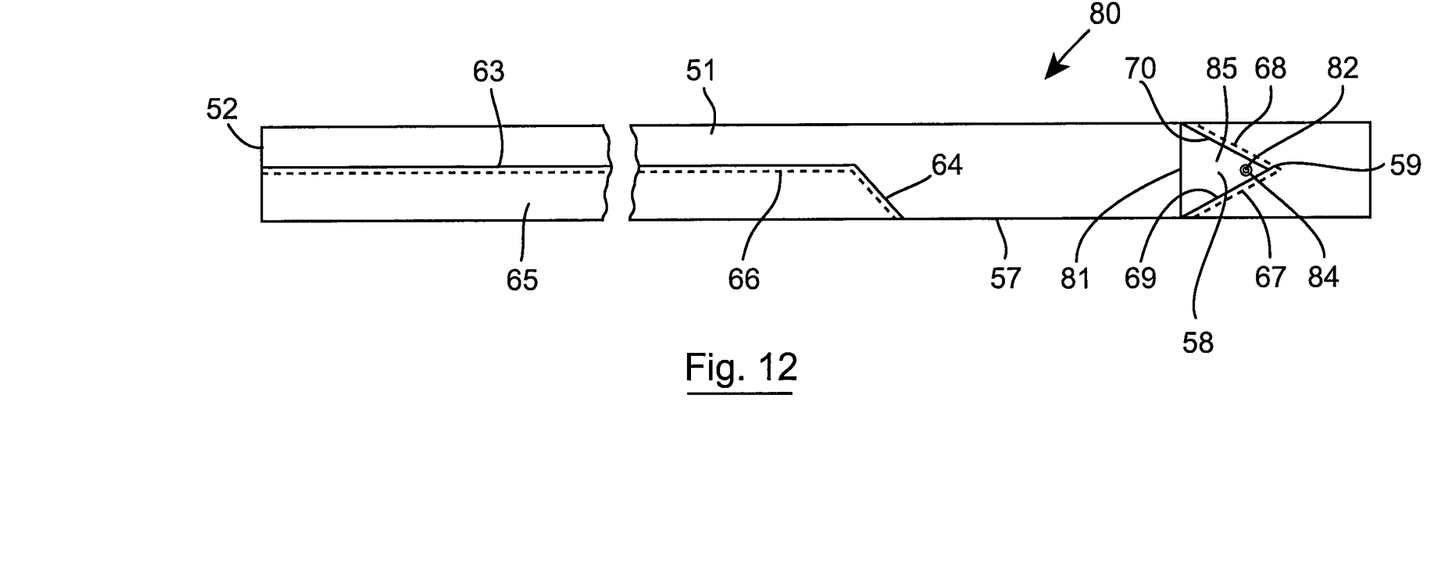
FIG. 12 is a side elevational view of the device of FIG. 11 in a state of being manufactured.

Referring now to FIGS. 11 and 12, there is illustrated a device also according to the invention, indicated generally by the reference numeral 80, for protecting a balloon catheter similar to the balloon catheter 2 of FIGS. 1 to 4 from contamination by bodily fluids and other bodily matter during use so that the balloon catheter 2 can be reused. The device 80 is substantially similar to the device 50 and similar components are identified by the same reference numerals. The main difference between the device 80 and the device 50 is that the device 80 is adapted for use with a guide wire externally of the device. Thus, in this embodiment of the invention, after the device 80 has been formed from an elongated tube, similar to the elongated tube 62, a further transverse heat seal weld line 81 is formed extending transversely across the elongated tube between the distal end of the balloon accommodating portion 57 and the proximal end of the converging distal end portion 58. The heat seal weld line 81 sealably closes the balloon accommodating portion 57 and in turn the hollow interior region 54 of the sheath 51. The converging distal end portion 58 in this embodiment of the invention is provided with a guide wire engaging bore 82 extending through an eyelet 84 secured in the converging distal end portion 58 so that the converging distal end portion 58 acts as a tab 85, which is substantially similar to the tab 31 of the device 30 to form an engagement element. Thus, when the distal end portion 58 is bent along the heat seal weld line 81 at 90° relative to the central axis of the balloon accommodating portion 57, the converging distal end portion 58 forms the tab 85 with the bore 82 aligned to engage a guide wire externally of the device 80.

Use of the device 80 in conjunction with a guide wire and a balloon catheter is similar to that already described with reference to the device 30.

Figure 13:
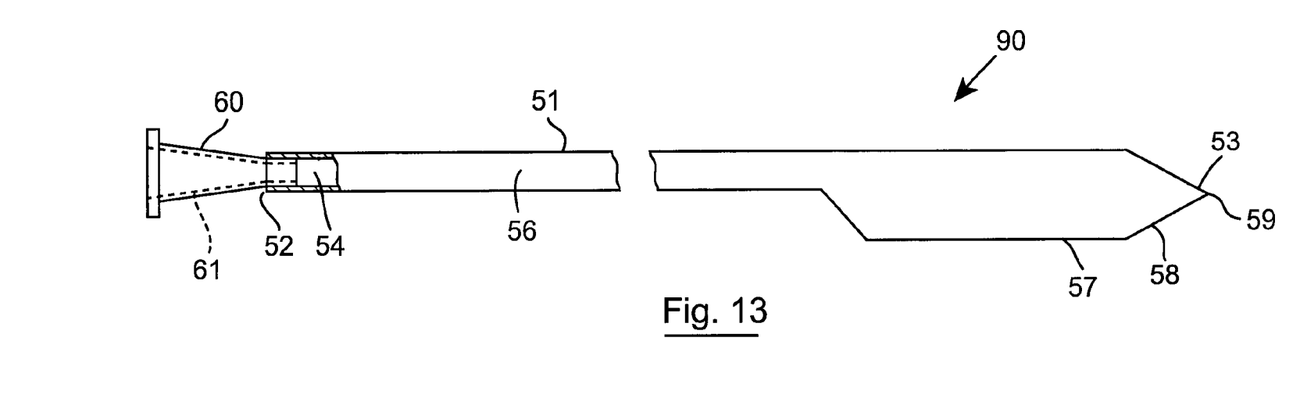
FIG. 13 is a top plan view of a device according to another embodiment of the invention for protecting a balloon catheter.
Figures 14, 15:
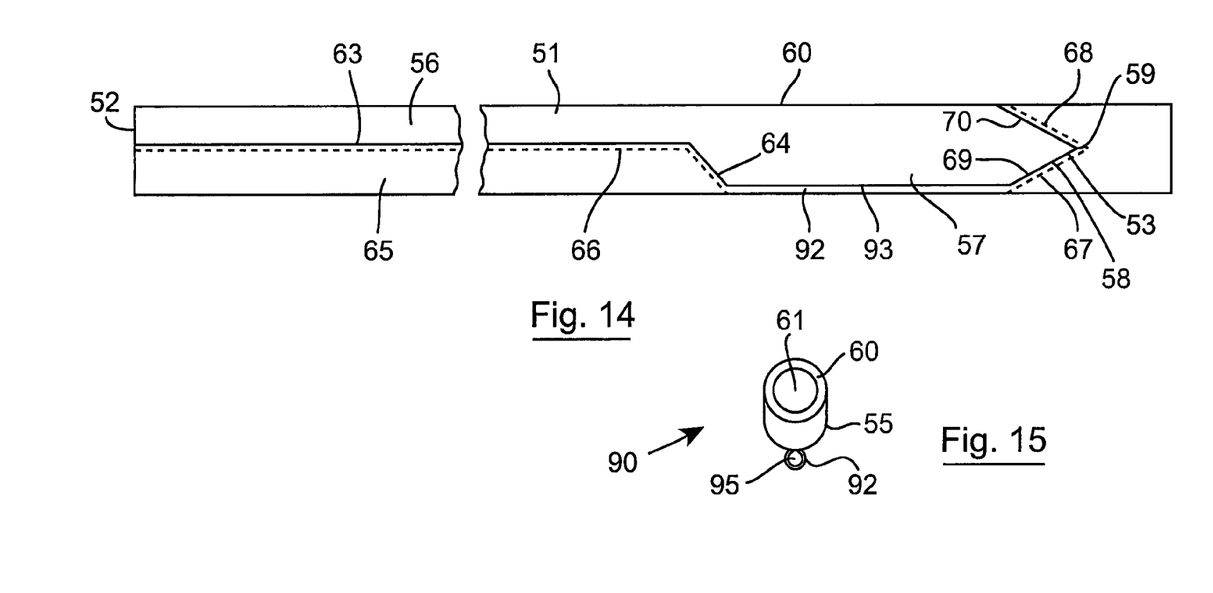
FIG. 14 is a top plan view of the device of FIG. 13 in a state of being manufactured.
FIG. 15 is an end elevational view of the device of FIG. 13.

Referring now to FIGS. 13 to 15, there is illustrated a device according to a further embodiment of the invention, indicated generally by the reference numeral 90, also for protecting a balloon catheter similar to the balloon catheter of FIGS. 1 to 4 from contamination by bodily fluids and other bodily matter during use, so that the balloon catheter 2 can be reused. The device 90 is substantially similar to the device 50, and similar components are identified by the same reference numerals. The device 90 is formed from an elongated tube similar to the tube 62. However, in this embodiment of the invention the device 90 is provided for use with a guide wire, similar to the guide wire 7, externally of the device 90. An engagement element 92 to externally engage the guide wire is formed in the tube 60 adjacent the balloon accommodating portion 57 by a heat seal weld line 93 which seals the guide wire accommodating element 92 from the balloon accommodating portion 57, thereby sealing the balloon accommodating portion 57, and in turn the hollow interior region 54. However, in this embodiment of the invention the inclined portion 64 of the heat seal weld line 63 and the heat weld line 69 terminate at the heat weld line 93, so that the engagement element 92 defines an elongated guide wire accommodating bore 95 extending parallel to and along the balloon accommodating portion 57, and externally thereof, for slideably engaging the guide wire.

Otherwise, the device 90 is similar to the device 50, and use of the device 90 is similar to use of the device 30 of FIGS. 5 to 8, whereby once the guide wire has been urged through a lumen, vessel or vascular system of the human or animal body to a remote site, the device 90 with the balloon catheter 2 located in the hollow interior region 54 of the sheath 51, and thus sheathed by the sheath 51 is then engaged on the proximal end of the guide wire 7 by engaging the guide wire accommodating bore 95 on the guide wire 7. The sheathed balloon catheter is then urged along the guide wire with the guide wire accommodating bore 95 of the engagement element 92 slideably engaging the guide wire 7 until the balloon of the sheathed balloon catheter 2 is located at the remote site.

Otherwise, the device 90 is similar to the device 50, and its use is similar to that of the device 30.

While the devices 1, 30, 50, 80 and 90 have been described for use with a balloon catheter, it is envisaged, in certain cases, that the sheath of the devices 1, 30, 50, 80 and 90 may be provided for use with a non-balloon catheter, in other words, a catheter which is provided without a balloon. In which case the balloon accommodating portion of the sheaths may be omitted.

It will also be appreciated that the balloon accommodating portion of the sheaths will be provided at a location along the sheath corresponding to the location of the balloon on the balloon catheter. It is also envisaged that where a balloon catheter is provided with more than one balloon and the balloons are spaced apart along the catheter, an appropriate number of similarly spaced apart balloon accommodating portions would be provided along the sheaths, in order to accommodate the respective balloons. In certain cases a single balloon accommodating portion may be provided to accommodate a plurality of balloons of a balloon catheter, even where the balloons are spaced apart along the balloon catheter.

While the devices 1, 30, 50, 80 and 90 have been described for use with a balloon catheter of the type disclosed in PCT Published Application Specifications Nos. WO 2009/001325 and WO 2009/001328, which are balloon catheters typically for use in determining the volume of a lumen or vessel or the transverse cross-sectional area of a lumen or vessel, for example, the oesophagus, the oesophageal sphincter, the stomach or a portion thereof formed by bariatric surgery, it is envisaged that the devices 1, 30, 50, 80 and 90 may be provided for use with any other types of balloon catheters, for example, a balloon catheter of the type for dilating a lumen, a portion of a lumen, a vessel or a portion thereof, for example, the oesophagus, or for ablating tissue in a lumen or vessel, such as the oesophagus. The devices 1, 30, 50, 80 and 90 may also be provided for protecting a balloon catheter for dilating an occlusion in a lumen or a vessel, for example, in a blood vessel of the cardiovascular system or an occlusion in the oesophagus, and the devices 1, 30, 50, 80 and 90 may also be provided for protecting a balloon catheter of the type used for determining the volume of a blood vessel or a cavity of the heart, or for any other purpose. It is also envisaged that the devices 1, 30, 50, 80 and 90 may be used in conjunction with a balloon catheter of the type for determining the distensibility of a sphincter, lumen or vessel.

While the sheath of the devices 1, 30, 50, 80 and 90 have been described as being of a particular type of film material, and of a particular material thickness, any other suitable type of material and suitable thickness of material may be used.

While the devices 30 and 80 have has been described as comprising a single guide wire engaging tab located at the distal end of the sheath, it is envisaged that in certain cases, a plurality of guide wire engaging tabs may be provided at spaced apart intervals along the length of the sheath, or at least along the length of a distal portion thereof, for engaging the guide wire at spaced apart intervals. Each tab would be provided with a guide wire engaging bore, which typically, may be formed by an eyelet or otherwise. Additionally, while the guide wire engaging means has been described as comprising a tab, any other suitable guide wire engaging means for engaging a guide wire externally of the sheath may be provided.

It will also be appreciated that while the sheath of the devices 1, 30, 50, 80 and 90 have been described as comprising a balloon accommodating portion, where the devices are to be used with a non-balloon catheter, the balloon accommodating portion may be dispensed with.

While the majority of the devices for protecting a balloon catheter have been described as comprising an engagement means for either internally or externally engaging a guide wire, in certain cases, it is envisaged that the devices for protecting a balloon catheter may be provided without an engagement means for engaging a guide wire, either internally or externally of the device.

The invention claimed is:

1. A combination comprising a balloon catheter, and a device for protecting the balloon catheter, the balloon catheter comprising:
an elongated catheter extending from a proximal end to a distal end, and a balloon located on the catheter adjacent the distal end thereof,
the device comprising an elongated sheath extending between a proximal end and a closed distal end and defining a hollow interior region, the proximal end of the sheath defining a proximal opening to the hollow interior region, the sheath defining a balloon accommodating portion and a catheter accommodating portion extending from the balloon accommodating portion to the proximal end of the sheath, the balloon catheter being located in the hollow interior region with the balloon located in the balloon accommodating portion and the catheter located in the catheter accommodating portion, the balloon accommodating portion of the sheath being configured to be urgeable by the balloon of the balloon catheter from a collapsed state with the balloon of the balloon catheter deflated to an erect state with the balloon of the balloon catheter inflated to a predefined maximum volume, the balloon accommodating portion having a circumferential length sufficient to accommodate unimpeded inflating of the balloon to the predefined maximum volume with substantially no stretching of the balloon accommodating portion, and the catheter accommodating portion being adapted to accommodate the catheter of the balloon catheter therein and to accommodate the balloon of the balloon catheter therethrough into the balloon accommodating portion with the balloon of the balloon catheter deflated, so that with the balloon deflated on the balloon catheter, the balloon is urgeable through the catheter accommodating portion into the balloon accommodating portion.

2. A combination as claimed in claim 1 in which the balloon accommodating portion is located to accommodate the balloon of the balloon catheter when the balloon catheter is fully located in the sheath.

3. A combination as claimed in claim 1 in which the balloon accommodating portion and the catheter accommodating portion are of a similar material, and are integrally formed.

4. A combination as claimed in claim 1 in which the sheath is adapted to internally accommodate a guide wire through the proximal opening into the hollow interior region of the sheath with the distal end of the guide wire located adjacent the distal end of the sheath.

5. A combination as claimed in claim 1 in which the balloon accommodating portion is located adjacent the distal end of the sheath.

6. A combination as claimed in claim 1 in which the catheter accommodating portion of the sheath is adapted to slideably accommodate the balloon catheter therein for accommodating the balloon of the balloon catheter with the balloon deflated into the balloon accommodating portion of the sheath.

7. A combination as claimed in claim 1 in which the sheath is of a material configurable to adopt a transverse cross-section of shape substantially similar to the shape of the transverse cross-section of the balloon catheter.

8. A combination as claimed in claim 1 in which the sheath is of a material configurable to define an elongated bore through which the balloon catheter is longitudinally slideable from the proximal opening to the distal end of the sheath.

9. A combination as claimed in claim 1 in which the sheath is of a flexible material.

10. A combination as claimed in claim 1 in which the balloon accommodating portion is of a material configurable to adopt a transverse cross-section of shape substantially similar to the shape of the transverse cross-section adopted by the balloon of the balloon catheter when inflated.

11. A combination as claimed in claim 1 in which the transverse cross-section of the balloon accommodating portion when adopting the shape substantially similar to the shape of the transverse cross-section of the balloon when inflated to the maximum predefined volume is of transverse cross-section which is equal to the transverse cross-section of the balloon when inflated to the predefined maximum volume.

12. A combination as claimed in claim 1 in which the sheath is of a film material.

13. A combination as claimed in claim 1 in which the film material of the sheath is of thickness in the range of 25 microns to 75 microns.

14. A combination as claimed in claim 1 in which the balloon accommodating portion of the sheath is of axial length greater than the axial length of the balloon of the balloon catheter.

15. A combination as claimed in claim 1 in which the sheath comprises a locating means adjacent the distal end thereof for locating the distal end of the guide wire adjacent the distal end of the sheath.

16. A combination as claimed in claim 1 further comprising a guide wire.

17. A combination as claimed in claim 16 in which the locating means comprises a distal portion of the sheath of transverse cross-sectional area adapted to releasably engage the distal end of the guide wire.

18. A combination as claimed in claim 16 in which the sheath is adapted to accommodate the balloon catheter being passed through the sheath along the guide wire located in the sheath.

19. A combination as claimed in claim 16 in which the sheath comprises an engagement means adapted for slideably engaging the guide wire externally of the sheath.

20. A combination as claimed in claim 19 in which the engagement means comprises an engagement element having a guide wire accommodating opening extending therethrough for slideably engaging a guide wire.

* * * * *